(12) United States Patent
Namba et al.

(10) Patent No.: US 9,145,310 B2
(45) Date of Patent: Sep. 29, 2015

(54) SEAWATER DESALINATION APPARATUS

(75) Inventors: Ryo Namba, Fuchu (JP); Katsuya Yokokawa, Fuchu (JP); Hideaki Yamagata, Urayasu (JP); Koichi Matsui, Tokyo (JP); Futoshi Kurokawa, Tachikawa (JP); Takeshi Matsushiro, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 95 days.

(21) Appl. No.: 13/104,756

(22) Filed: May 10, 2011

(65) Prior Publication Data

US 2011/0278208 A1 Nov. 17, 2011

(30) Foreign Application Priority Data

May 17, 2010 (JP) ................................ 2010-113535

(51) Int. Cl.
| | | |
|---|---|---|
| B01D 35/00 | (2006.01) | |
| B01D 21/24 | (2006.01) | |
| G01N 31/00 | (2006.01) | |
| C02F 1/44 | (2006.01) | |
| G01N 31/22 | (2006.01) | |
| B01D 61/06 | (2006.01) | |
| B01D 69/12 | (2006.01) | |
| B01D 61/02 | (2006.01) | |
| C02F 103/08 | (2006.01) | |

(52) U.S. Cl.
CPC ............... *C02F 1/441* (2013.01); *B01D 61/06* (2013.01); *B01D 69/12* (2013.01); *G01N 31/221* (2013.01); *B01D 61/02* (2013.01); *B01D 2311/04* (2013.01); *B01D 2311/08* (2013.01); *C02F 2103/08* (2013.01); *C02F 2209/005* (2013.01); *C02F 2209/03* (2013.01); *C02F 2209/40* (2013.01); *C02F 2303/10* (2013.01); *Y02W 10/30* (2015.05)

(58) Field of Classification Search
None
See application file for complete search history.

(56) References Cited

U.S. PATENT DOCUMENTS

| | | | | |
|---|---|---|---|---|
| 3,774,763 A | * | 11/1973 | Yall et al. ..................... | 210/96.2 |
| 4,724,079 A | * | 2/1988 | Sale et al. ..................... | 210/638 |
| 5,049,045 A | * | 9/1991 | Oklejas et al. ................ | 417/365 |

(Continued)

FOREIGN PATENT DOCUMENTS

| | | |
|---|---|---|
| JP | 64-11610 | 1/1989 |
| JP | 7-284637 | 10/1995 |

(Continued)

OTHER PUBLICATIONS

First Office Action, mailed Apr. 24, 2012, from the Japanese Patent Office in corresponding Japanese Patent Application No. 2010-113535, and English translation thereof (6 pages).

*Primary Examiner* — Nam Nguyen
*Assistant Examiner* — Richard Gurtowski
(74) *Attorney, Agent, or Firm* — Finnegan, Henderson, Farabow, Garrett & Dunner, LLP

(57) ABSTRACT

According to one embodiment, a seawater desalination apparatus includes a pressure sensor configured to measure a pressure of seawater which is supplied to a reverse osmosis membrane that is configured to separate seawater into fresh water and condensed seawater and to discharge the fresh water and the condensed seawater, a sensor configured to measure a flow amount of the fresh water which is discharged from the reverse osmosis membrane, a sensor configured to measure a flow amount of the condensed seawater discharged from the reverse osmosis membrane or a flow amount of the seawater discharged from a booster pump, a sensor configured to measure a flow amount of the seawater which is supplied to a power recovery device, and a controller configured to execute control based on values measured by the sensors.

7 Claims, 3 Drawing Sheets

(56) References Cited

U.S. PATENT DOCUMENTS

| | | | |
|---|---|---|---|
| 6,139,740 A * | 10/2000 | Oklejas | 210/321.66 |
| 6,332,110 B1 * | 12/2001 | Wolfe | 702/22 |
| 2008/0093282 A1 * | 4/2008 | Ukon | 210/192 |

FOREIGN PATENT DOCUMENTS

| | | |
|---|---|---|
| JP | 2009-154070 | 7/2009 |
| JP | 2009-279472 | 12/2009 |
| JP | 2010-63976 | 3/2010 |

* cited by examiner

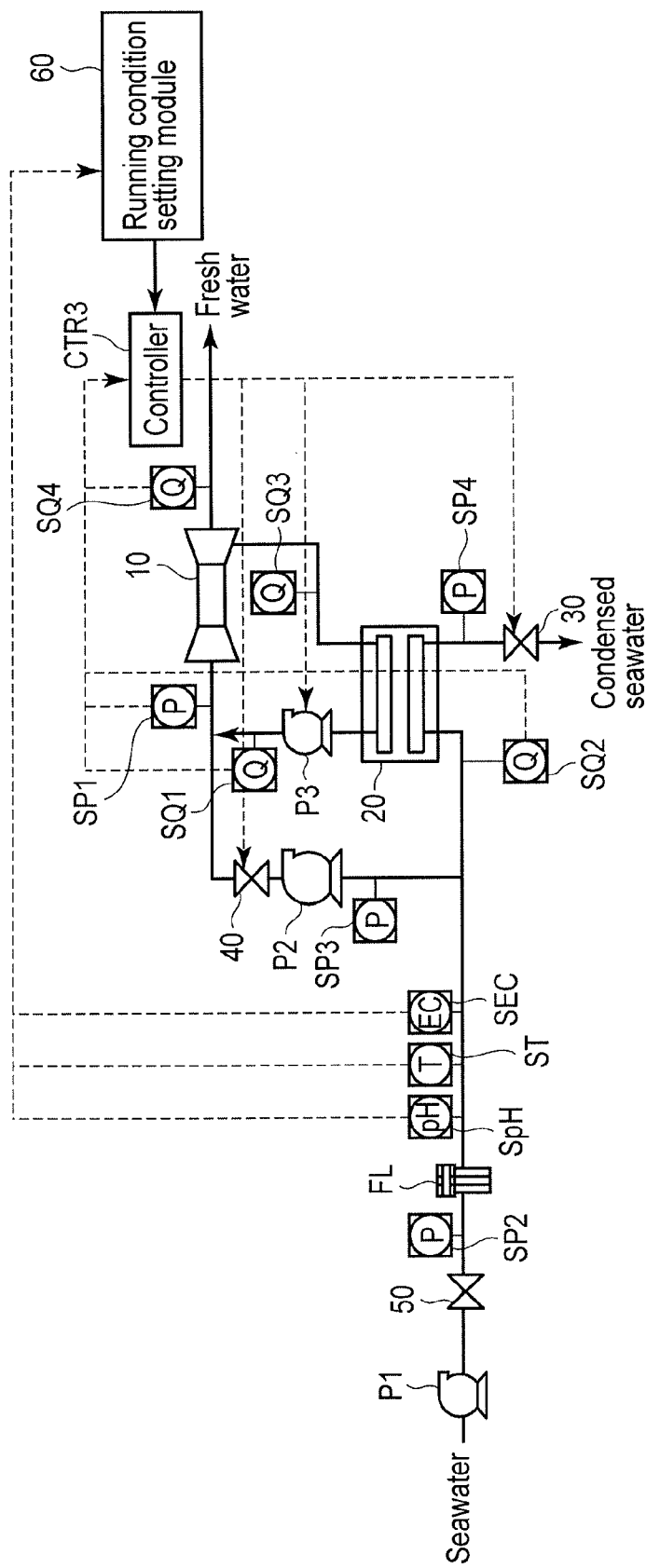
F I G. 5

SEAWATER DESALINATION APPARATUS

CROSS-REFERENCE TO RELATED APPLICATIONS

This application is based upon and claims the benefit of priority from Japanese Patent Application No. 2010-113535, filed May 17, 2010; the entire contents of which are incorporated herein by reference.

FIELD

Embodiments described herein relate generally to a seawater desalination apparatus.

BACKGROUND

With water problems becoming more and more serious on a global scale, the competition in water business is on the increase worldwide, considering the market of water business as a huge one. In Middle Eastern countries which do not have surface water, such as rivers, or ground water, as water sources, or in regions within the country where a drought risk is high, seawater desalination technologies for securing water sources have been introduced, and large-scale seawater desalination plants have been installed.

The dominant conventional seawater desalination technology is an evaporation method in which seawater is first heated and evaporated and then condensation and recovery are performed. In recent years, on the other hand, a method using an RO (reverse osmosis) membrane (hereinafter referred to as "reverse osmosis membrane") has been gaining in popularity from the standpoint of economic efficiency.

BRIEF DESCRIPTION OF THE DRAWINGS

FIG. 5 schematically shows an example of the structure of a seawater desalination apparatus according to a third embodiment.

DETAILED DESCRIPTION

In general, according to one embodiment, a seawater desalination apparatus comprises a reverse osmosis membrane configured to separate seawater into fresh water and condensed seawater and to discharge the fresh water and the condensed seawater; a high-pressure pump configured to feed seawater to the reverse osmosis membrane; a power recovery device to which the seawater and the condensed seawater discharged from the reverse osmosis membrane are supplied, and which is configured to discharge the seawater at a high pressure by pressure energy recovered from the condensed seawater and to exhaust the condensed seawater at a low pressure; a booster pump configured to boost the seawater discharged from the power recovery device up to a pressure equal to a pressure of the seawater discharged from the high-pressure pump, and to discharge the boosted seawater such that the boosted seawater mixes in the seawater which is discharged from the high-pressure pump; an exhaust valve configured to control an amount of the condensed seawater which is discharged from the power recovery device; a pressure sensor configured to measure a pressure of the seawater which is supplied to the reverse osmosis membrane; a first flow-amount sensor configured to measure a flow amount of the fresh water which is discharged from the reverse osmosis membrane; a second flow-amount sensor configured to measure a flow amount of the condensed seawater discharged from the reverse osmosis membrane or a flow amount of the seawater discharged from the booster pump; a third flow-amount sensor configured to measure a flow amount of the seawater which is supplied to the power recovery device; and a controller configured to control a number of revolutions of the high-pressure pump, based on values measured by the pressure sensor and the first flow-amount sensor, to control a number of revolutions of the booster pump, based on a value measured by the second flow-amount sensor, and to control a valve opening degree of the exhaust valve, based on values measured by the second flow-amount sensor and the third flow-amount sensor.

A seawater desalination apparatus according to an embodiment will now be described in detail with reference to the accompanying drawings.

Figure 1:
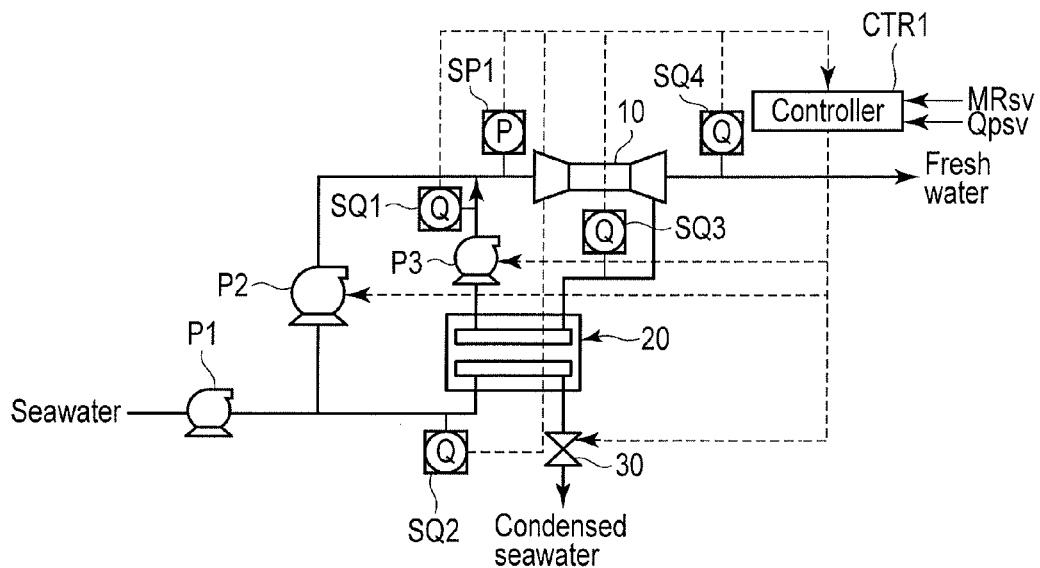
FIG. 1 schematically shows an example of the structure of a seawater desalination apparatus according to a first embodiment.

FIG. 1 schematically shows a structure example of a seawater desalination apparatus according to a first embodiment. The seawater desalination apparatus according to this embodiment comprises a water feed pump P1, a high-pressure pump P2, a booster pump P3, a power recovery device 20, a brine flow-amount control valve 30, a reverse osmosis membrane 10, a controller CTR1, a pressure sensor SP1, and flow-amount sensors SQ1, SQ2, SQ3 and SQ4.

The water feed pump P1 sucks seawater from a pre-process system (not shown), and feeds seawater into the seawater desalination apparatus. The seawater, which has been discharged from the feed pump P1, is supplied to the high-pressure pump P2 and power recovery device 20.

The high-pressure pump P2 boosts the seawater, which has been supplied from the water feed pump P1, up to a high-pressure state (e.g. about 6 MPa), and discharges the high-pressure seawater. The seawater, which has been discharged from the high-pressure pump P2, is supplied to the reverse osmosis membrane 10.

The reverse osmosis membrane 10 filters the seawater to remove a salt content from the seawater, and generates fresh water. The salt content, which has been removed by the reverse osmosis membrane 10, is drained as condensed seawater. The condensed seawater, which has been drained from the reverse osmosis membrane 10, is supplied to the power recovery device 20.

Figure 2:
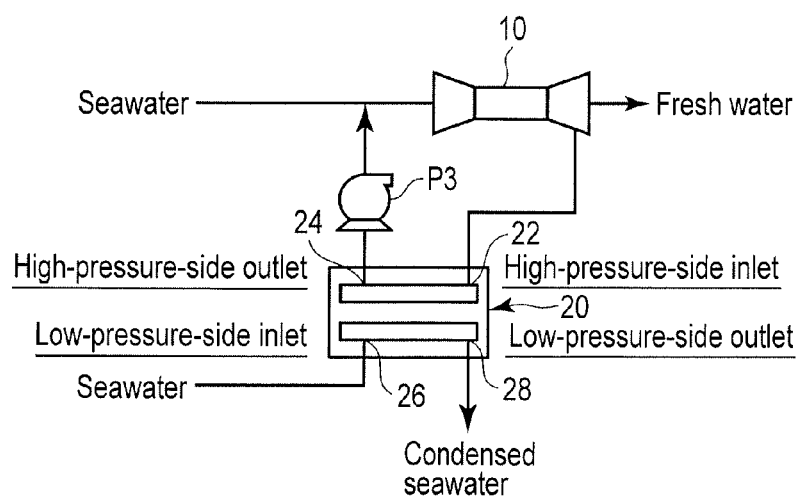
FIG. 2 is a view for describing a structure example of a power recovery device of the seawater desalination apparatus shown in FIG. 1.

FIG. 2 shows a structure example of the power recovery device 20. In the present embodiment, the power recovery device 20 is, for example, a volume-type power recovery device. The power recovery device 20 comprises a high-pressure-side inlet 22, a high-pressure-side outlet 24, a low-pressure-side inlet 26 and a low-pressure-side outlet 28.

The power recovery device 20 boosts the seawater, which flows in via the low-pressure-side inlet 26 from the water feed pump P1, by making use of pressure energy included in condensed seawater, and outputs the seawater to the booster pump P3. The power recovery device 20 drains the condensed seawater, from which the pressure energy has been recovered, via the low-pressure-side outlet 28 and exhaust valve 30.

Specifically, the condensed seawater, which has been drained from the reverse osmosis membrane 10, is supplied to the high-pressure-side inlet 22. The condensed seawater, after the pressure energy thereof has been recovered, is drained from the low-pressure-side outlet 28. Seawater is supplied from the water feed pump P1 to the low-pressure-side inlet 26. This seawater is discharged from the high-pressure-side outlet 24 by making use of the pressure (power) which the condensed sweater has. The seawater, which has been discharged from the high-pressure-side outlet 24, is supplied to the booster pump P3.

The exhaust valve 30 is, for example, a brine flow-amount control valve, and is disposed as an actuator in order to control the flow amount of the condensed seawater. The valve opening degree of the exhaust valve 30 is controlled by a control signal from the controller CTR1.

The booster pump P3 boosts the seawater from the power recovery device 20 up to a pressure which is substantially equal to the pressure of the seawater from the high-pressure pump P2. The boosted seawater, which has been discharged from the booster pump P3, is mixed in the seawater from the high-pressure pump P2, and fed to the reverse osmosis membrane 10.

The pressure sensor SP1 measures the inlet pressure of the reverse osmosis membrane 10. The flow-amount sensor SQ1 measures the output flow amount of the booster pump P3. The flow-amount sensor SQ2 measures the inflow amount of seawater into the low-pressure-side inlet 26 of the power recovery device 20. The flow-amount sensor SQ3 measures the inflow amount of condensed seawater into the high-pressure-side inlet 22 of the power recovery device 20. The flow-amount sensor SQ4 measures the output flow amount of the reverse osmosis membrane 10. The values measured by the pressure sensor SP1 and flow-amount sensors SQ1 to SQ4 are delivered to the controller CTR1.

The controller CTR1 is configured to control the number of revolutions of the high-pressure pump P2 on the basis of the values measured by the pressure sensor SP1 and flow-amount sensor SQ4, to control the number of revolutions of the booster pump P3 on the basis of the value measured by the flow-amount sensor SQ1 or flow-amount sensor SQ3, and to control the valve opening degree of the exhaust valve 30 on the basis of the values measured by the flow-amount sensor SQ2 and flow-amount sensor SQ1 or the values measured by the flow-amount sensor SQ2 and flow-amount sensor SQ3.

Next, the operation of the above-described seawater desalination apparatus is described.

In order to set the fresh water production amount at a desired flow amount, the controller CTR1 controls the operation of the high-pressure pump P2, thereby applying a pressure, which is higher than the osmotic pressure by the seawater salt content, to the reverse osmosis membrane 10. Since the production amount of fresh water depends greatly on the number of revolutions of the high-pressure pump P2, the controller CTR1 controls the number of revolutions of the high-pressure pump P2, for example, by PID (P: Proportional, I: Integral, D: Differential), so that the measured value of the fresh water production amount may agree with a preset target value.

On the other, the inlet pressure of the reverse osmosis membrane 10 is constantly monitored by the pressure sensor SP1 so that the inlet pressure of the reverse osmosis membrane 10 may not become a withstand pressure or more of the reverse osmosis membrane 10. The controller CTR1 controls the number of revolutions of the high-pressure pump P2 so that the value measured by the pressure sensor SP1 may not become a predetermined value or more.

The controller CTR1 calculates a flow amount of condensed seawater, based on a desired recovery ratio, calculates an amount (target flow amount) of seawater which is fed out from the booster pump P3, and controls the number of revolutions of the booster pump P3 so that the target flow amount may agree with the amount of seawater which is fed out from the booster pump P3. When the target flow amount Qhbsv is calculated from the set recovery ratio MRsv, the target flow amount Qhbsv is calculated, as shown below, by using a fresh water production amount set value Qpsv which is a set value for use in control of the high-pressure pump P2:

$$Qhbsv = Qpsv \times (100/MRsv - 1),$$

where Mrsv≠0.

In addition, the controller CTR1 sets a difference between the flow amount of the high-pressure-side inlet 22 of the power recovery device 20 and the flow amount of the low-pressure-side inlet 26 at a predetermined value. By this control, the capability of the power recovery device 20 can be exhibited, and the power consumption in the power recovery device 20 can effectively be reduced. The flow amount of the high-pressure-side inlet 22 of the power recovery device 20 is controlled by the booster pump P3. The flow amount of the low-pressure-side outlet 28 is controlled by the exhaust valve 30.

For example, in the case where the brine flow-amount control valve and rotary volume-type power recovery device are adopted, a lubrication water amount necessary for rotation is taken into account, and the brine flow-amount control valve is controlled by setting a flow amount, which is greater by the lubrication water amount, as a measurement value of the high-pressure-side condensed seawater flow amount and a target value of the low-pressure-side condensed seawater flow amount.

As has been described above, the pressure sensor SP1 and flow-amount sensors SQ1, SQ2, SQ3 and SQ4 are disposed and the controller CTR1 controls the high-pressure pump P2, booster pump P3 and exhaust valve 30. Thereby, there can be provided a seawater desalination apparatus in which proper running conditions of the power recovery device are set and the electric power amount is reduced.

Figure 3:
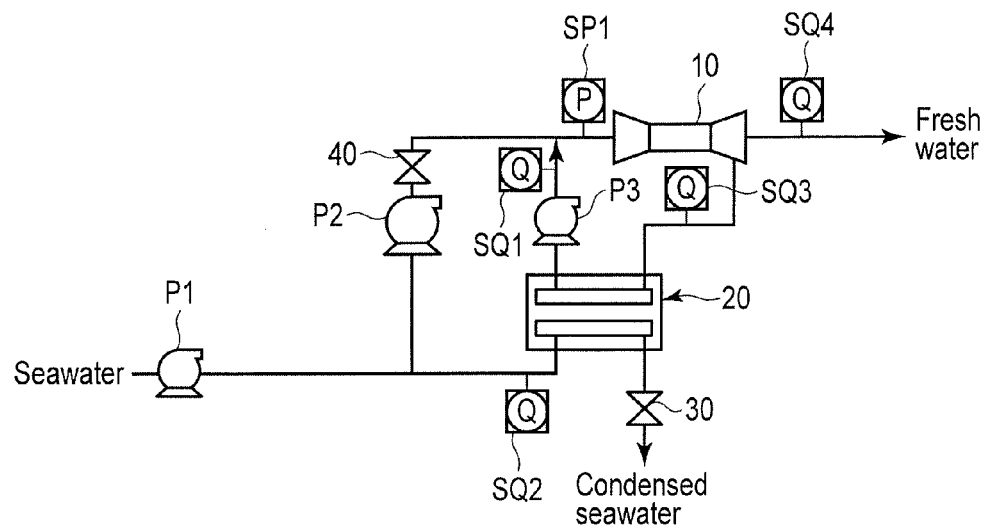
FIG. 3 schematically shows another example of the structure of the seawater desalination apparatus according to the first embodiment.

FIG. 3 shows a structure example of the seawater desalination apparatus in the case where the number of revolutions of the high-pressure pump 2 is fixed. In this case, the seawater desalination apparatus includes a high-pressure pump discharge valve 40 which is disposed at the rear stage of the high-pressure pump P2.

The controller CTR1 controls the valve opening degree of the high-pressure pump discharge valve 40 so as to set the fresh water production amount at a predetermined value, based on the values measured by the pressure sensor SP1 and flow-amount sensor SQ4. In addition, where necessary, the controller CTR1 controls the valve opening degree of the high-pressure pump discharge valve 40 so that the inlet pressure of the reverse osmosis membrane 10 may not become a withstand pressure or more of the reverse osmosis membrane 10.

In this manner, the pressure sensor SP1 and flow-amount sensors SQ1, SQ2, SQ3 and SQ4 may be disposed and the controller CTR1 may control the high-pressure pump discharge valve 40, booster pump P3 and exhaust valve 30. Thereby, there can be provided a seawater desalination apparatus in which proper running conditions are set according to conditions of water quality, production water amount, etc., and the electric power amount is reduced. As a result, the fresh water generation cost (yen/$m^3$) can be reduced.

Next, a seawater desalination apparatus according to a second embodiment is described with reference to the drawings. In the description below, the same structural parts as in the seawater desalination apparatus according to the above-described first embodiment are denoted by like reference numerals, and a description thereof is omitted.

Figure 4:
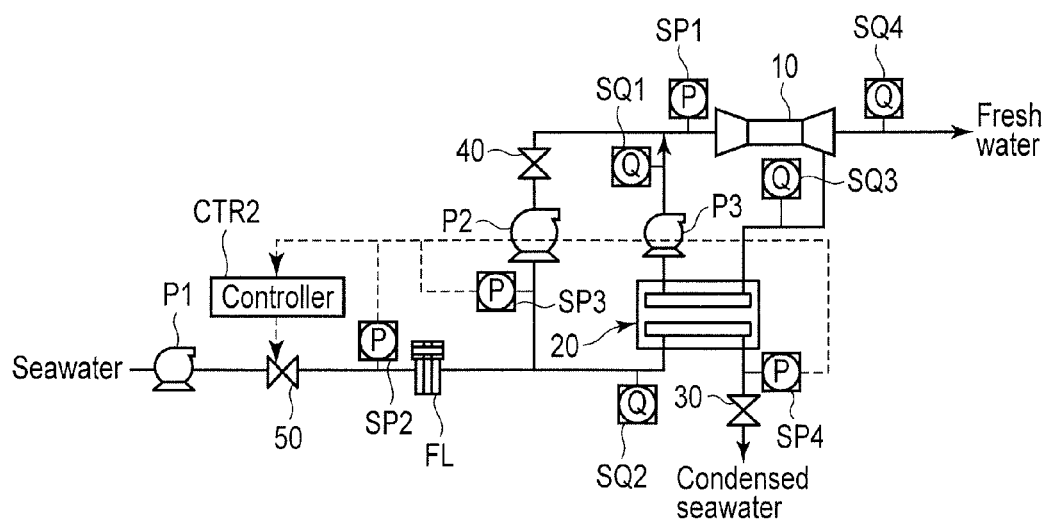
FIG. 4 schematically shows an example of the structure of a seawater desalination apparatus according to a second embodiment.

FIG. 4 schematically shows a structure example of the seawater desalination apparatus according to the present embodiment. The seawater desalination apparatus according to this embodiment further comprises a water feed pressure control valve 50, a protection filter FL, a high-pressure pump discharge valve 40, pressure sensors SP2, SP3 and SP4, and a controller CTR2.

In the meantime, the seawater desalination apparatus according to the present embodiment further includes a controller (not shown) which controls the valve opening degree of the discharge valve 40, the number of revolutions of the booster pump P3 and the valve opening degree of the exhaust valve 30, on the basis of the values measured by the pressure sensor SP1 and the flow-amount sensors SQ1, SQ2, SQ3 and SQ4.

Like the case shown in FIG. 3, this controller controls the valve opening degree of the high-pressure pump discharge valve 40 so as to set the fresh water production amount at a predetermined value, based on the values measured by the pressure sensor SP1 and flow-amount sensor SQ4. In addition, the controller, which is not shown, controls the number of revolutions of the booster pump P3, based on the value measured by the flow-amount sensor SQ1 or flow-amount sensor SQ3. Besides, the controller, not shown, controls the valve opening degree of the exhaust valve 30 on the basis of the values measured by the flow-amount sensor SQ2 and flow-amount sensor SQ1 or the values measured by the flow-amount sensor SQ2 and flow-amount sensor SQ3.

The protection filter FL is provided at the rear stage of the water feed pump P1. The protection filter FL protects the reverse osmosis membrane 10 by removing suspended matter from seawater which is fed from a regulating bath (not shown). In this case, the water feed pressure control valve 50 is provided at the rear stage of the water feed pump P1 and at the front stage of the protection filter FL.

The pressure sensor SP2 is provided at the rear stage of the water feed pressure control valve 50 and at the front stage of the protection filter FL. The pressure sensor SP2 measures the pressure of the seawater which is discharged from the water feed pressure control valve 50 to the protection filter FL.

The pressure sensor SP3 is provided at the rear stage of the protection filter FL and at the front stage of the high-pressure pump P2. The pressure sensor SP3 measures the pressure of the seawater which is supplied to the high-pressure pump S2 via the protection filter FL.

The pressure sensor SP4 is disposed between the low-pressure-side outlet 28 of the power recovery device 20 and the exhaust valve 30. The pressure sensor SP4 measures the pressure of the seawater which is drained from the low-pressure-side outlet 28 of the power recovery device 20.

The controller CTR2 controls the valve opening degree of the water feed pressure control valve 50, based on the values measured by the pressure sensors SP2, SP3 and SP4. The controller CTR2 is configured to control the valve opening degree of the water feed pressure control valve 50, so that the inlet pressure of the protection filter FL may not become a withstand pressure or more of the protection filter FL. In addition, in order to protect the high-pressure pump P2, the controller CTR2 is configured to control the valve opening degree of the water feed pressure control valve 50 so that the suction pressure of the high-pressure pump P2 may not decrease below the lower limit value.

Depending on the material of the power recovery device 20, the back pressure may be measured by the pressure sensor SP4, and thereby the controller CTR2 can prevent a cavitation from occurring in the power recovery device 20 and prevent the apparatus from being broken. In this case, the controller CTR2 controls the valve opening degree of the water feed pressure control valve 50 so that the back pressure may become a preset value or more.

In this manner, even in the case where the protection filter FL is provided at the rear stage of the water feed pump P1, the pressure sensors SP2, SP3 and SP4 may further be disposed and the valve opening degree of the water feed pressure control valve 50 may be controlled. Thereby, like the above-described first embodiment, there can be provided a seawater desalination apparatus in which proper running conditions for the power recovery device are set, and the electric power amount is reduced. As a result, the fresh water generation cost (yen/m$^3$) can be reduced.

In the above-described embodiment, the controller CTR2 and the controller, which is not shown, are independently structured. However, the controller CTR2 and the controller, not shown, may be integrally structured. In this case, too, the same advantageous effects can be obtained.

Next, a seawater desalination apparatus according to a third embodiment is described with reference to the drawings.

FIG. 5 schematically shows a structure example of the seawater desalination apparatus according to the present embodiment. The seawater desalination apparatus according to this embodiment further comprises measuring devices which measure the water quality of raw seawater, an electric power amount meter (not shown) which measures electric power amounts of the high-pressure pump P2, booster pump P3 and water feed pump P1, and a running condition setting module 60. The seawater desalination apparatus comprises, as the measuring devices, a pH meter SpH which measures the pH of seawater, a thermometer ST which measures the temperature of seawater, and an electric conductivity meter SEC which measures the electric conductivity of seawater. The seawater desalination apparatus according to the present embodiment, like the above-described second embodiment, further comprises a controller (not shown) which controls the valve opening degree of the water feed pressure control valve 50, based on the values delivered from the pressure sensors SP2, SP3 and SP4.

The pH meter SpH is disposed at the rear stage of the protection filter FL and at the front stage of a branch point between conduits to the high-pressure pump P2 and power recovery device 20. The pH meter SpH measures the pH of seawater which has passed through the protection filter FL. The value measured by the pH meter SpH is delivered to the running condition setting module 60.

The thermometer ST is provided at the rear stage of the protection filter FL and at the front stage of the branch point between the conduits to the high-pressure pump P2 and power recovery device 20. The thermometer ST measures the temperature of seawater which has passed through the protection filter FL. The value measured by the thermometer ST is delivered to the running condition setting module 60.

The electric conductivity meter SEC is provided at the rear stage of the protection filter FL and at the front stage of the branch point between the conduits to the high-pressure pump P2 and power recovery device 20. The electric conductivity meter SEC measures the electric conductivity of seawater which has passed through the protection filter FL. The value measured by the electric conductivity meter SEC is delivered to the running condition setting module 60.

The running condition setting module 60 sets the running conditions of the seawater desalination apparatus, based on the values delivered from the pH meter SpH, thermometer ST and electric conductivity meter SEC. In the present embodiment, a target flow amount and a recovery ratio are set as the running conditions. The target flow amount is a target value of the flow amount of seawater which is discharged from the booster pump P3.

Based on the delivered values of the pH, temperature and electric conductivity, the running condition setting module 60 sets the recovery ratio and target flow amount, thereby to more reduce the power consumptions of the water feed pump P1, high-pressure pump P2 and booster pump P3.

The running condition setting module 60, for example, sets a predetermined recovery ratio, calculates the flow amount of condensed seawater, based on the recovery ratio, and calculates the amount of seawater (target flow amount) which is discharged from the booster pump P3. In the meantime, when the target flow amount Qhbsv is calculated from the set recovery ratio MRsv, the target flow amount Qhbsv is calculated, as shown below, by using a fresh water production amount set value Qpsv which is a set value for use in control of the high-pressure pump P2:

$$Qhbsv = Qpsv \times (100/MRsv - 1),$$

where Mrsv≠0.

In addition, the running condition setting module 60 increases the target flow amount and recovery ratio if the temperature value delivered from the thermometer ST becomes higher, and decreases the target flow amount and recovery ratio if the temperature value becomes lower. The running condition setting module 60 decreases the target flow amount and recovery ratio if the electric conductivity delivered from the electric conductivity meter SEC becomes higher, and increases the target flow amount and recovery ratio if the electric conductivity delivered from the electric conductivity meter SEC becomes lower. The running condition setting module 60 corrects the value of the electric conductivity of seawater, based on the value of the pH delivered from the pH meter SpH.

The target flow amount and recovery ratio, which have been set by the running condition setting module 60, are delivered to the controller CTR3.

The controller CTR3 controls the number of revolutions of the booster pump P3, the valve opening degree of the exhaust valve 30 and the valve opening degree of the discharge valve 40, thereby to achieve the target flow amount and recovery ratio which have been delivered. The controller CTR3 controls the number of rotations of the booster pump P3 so that the target flow amount may agree with the amount of seawater which is discharged from the booster pump P3.

In addition, the controller CTR3 sets a difference between the flow amount of the high-pressure-side inlet 22 of the power recovery device 20 and the flow amount of the low-pressure-side inlet 26 at a predetermined value. By this control, the capability of the power recovery device 20 can be exhibited, and the power consumption in the power recovery device 20 can effectively be reduced. The flow amount of the high-pressure-side inlet 22 of the power recovery device 20 is controlled by the booster pump P3. The flow amount of the low-pressure-side outlet 28 is controlled by the exhaust valve 30.

The seawater desalination apparatus according to this embodiment is configured to display, on a display (not shown), which is integral with the apparatus, or an externally connected monitor, the electric power amounts which are consumed by the water feed pump P1, high-pressure pump P2 and booster pump P3 and are measured by the electric power amount meter.

The efficiencies of the power recovery device 20 and pumps P1, P2 and P3 and the characteristics of the reverse osmosis membrane 10 at the time of operation of the apparatus vary in accordance with the running conditions such as the water quality of raw seawater and the recovery ratio. Accordingly, the total electric power amount per unit production water amount varies. The variation of the total electric power amount per unit production water amount can be visualized, for example, in the form of a table, a two-dimensional graph or a 3D (three-dimensional) graph. In addition, it is possible to realize the running function which minimizes the total electric power amount per unit production water amount, in association with each of the water quality conditions of raw seawater.

As has been described above, in the case where the measuring devices which measure the water quality of seawater are provided at the rear stage of the protection filter FL, there can be provided a seawater desalination apparatus in which more proper running conditions are set according to conditions of water quality, production water amount, etc., and the electric power amount is reduced. As a result, the fresh water generation cost (yen/m$^3$) can be reduced.

In the present embodiment, the pH meter SpH is provided, but the pH meter SpH may be dispensed with. Even in the case where the pH meter SpH is omitted, the same advantageous effects as the seawater desalination apparatus according to the above-described embodiment can be obtained. In addition, the controller CTR3 may be formed integral with the controller which is not shown. Also in this case, the same advantageous effects as the seawater desalination apparatus according to the above-described embodiment can be obtained.

Besides, in the present embodiment, the electric power amount meter is provided, but the electric power amount meter may be dispensed with. Even in the case where the electric power amount meter is omitted, the same advantageous effects as the seawater desalination apparatus according to the above-described embodiment can be obtained.

The present invention is not limited directly to the above-described embodiments. In practice, the structural elements can be modified and embodied without departing from the spirit of the invention. Various inventions can be made by properly combining the structural elements disclosed in the embodiments. For example, some structural elements may be omitted from all the structural elements disclosed in the embodiments. Furthermore, structural elements in different embodiments may properly be combined.

For example, in each of the above-described embodiments, it should suffice if one of the flow-amount sensor SQ1 and flow-amount sensor SQ3 is disposed, and either the flow-amount sensor SQ1 or flow-amount sensor SQ3 may be omitted. Even in this case, the same advantageous effects as the seawater desalination apparatus according to the above-described embodiment can be obtained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A seawater desalination apparatus comprising:
a reverse osmosis membrane configured to separate seawater into fresh water and condensed seawater and to discharge the fresh water and the condensed seawater;
a high-pressure pump configured to feed seawater to the reverse osmosis membrane;
a power recovery device to which the seawater and the condensed seawater discharged from the reverse osmosis membrane are supplied, and which is configured to discharge the seawater at a high pressure by pressure energy recovered from the condensed seawater and to exhaust the condensed seawater at a low pressure;
a booster pump configured to boost the seawater discharged from the power recovery device up to a pressure equal to a pressure of the seawater discharged from the high-pressure pump, and to discharge the boosted seawater such that the boosted seawater mixes in the seawater which is discharged from the high-pressure pump;
an exhaust valve configured to control an amount of the condensed seawater which is discharged from the power recovery device;
a pressure sensor configured to measure a pressure of the seawater which is supplied to the reverse osmosis membrane;
a first flow-amount sensor configured to measure a flow amount of the fresh water which is discharged from the reverse osmosis membrane;
a second flow-amount sensor configured to measure a flow amount of the condensed seawater discharged from the reverse osmosis membrane or a flow amount of the seawater discharged from the booster pump;
a third flow-amount sensor configured to measure a flow amount of the seawater which is supplied to the power recovery device;
a controller that:
controls a number of revolutions of the high-pressure pump, based on values measured by the pressure sensor and the first flow-amount sensor,
controls a number of revolutions of the booster pump, based on a value measured by the second flow-amount sensor,
controls a valve opening degree of the exhaust valve, based on values measured by the second flow-amount sensor and the third flow-amount sensor, and
controls the number of revolutions of the booster pump and the valve opening degree of the exhaust valve in such a manner that a difference between the flow amount of the condensed seawater supplied from the reverse osmosis membrane to the power recovery device and the flow amount of the seawater supplied to the power recovery device becomes a predetermined value, wherein the predetermined value is the power consumption of the power recovery device;
a thermometer configured to measure a temperature of seawater supplied to the high-pressure pump and the power recovery device;
an electrical conductivity meter configured to measure an electrical conductivity of the seawater supplied to the high-pressure pump and the power recovery device;
a pH meter configured to measure a pH of the seawater which is supplied to the high-pressure pump and the power recovery device, and
a setting module that:
sets a target flow amount of the booster pump and a recovery ratio, based on values measured by the thermometer and the electrical conductivity meter,
delivers the target flow amount and the recovery ratio to the controller, and
corrects the target flow amount and the recovery ratio, based on a value measured by the pH meter.

2. A seawater desalination apparatus comprising:
a reverse osmosis membrane configured to separate seawater into fresh water and condensed seawater and to discharge the fresh water and the condensed seawater;
a high-pressure pump configured to feed seawater;
a discharge valve disposed between the high-pressure pump and the reverse osmosis membrane and configured to control an amount of the seawater which is supplied from the high-pressure pump to the reverse osmosis membrane;
a power recovery device to which the seawater and the condensed seawater discharged from the reverse osmosis membrane are supplied, and which is configured to discharge the seawater at a high pressure by pressure energy recovered from the condensed seawater and to exhaust the condensed seawater at a low pressure;
a booster pump to which the seawater with the high pressure, which is discharged from the power recovery device, is supplied, and which is configured to boost the seawater with the high pressure up to a pressure equal to a pressure of the seawater discharged from the high-pressure pump, and to discharge the boosted seawater such that the boosted seawater mixes in the seawater which is discharged from the high-pressure pump;
an exhaust valve configured to control an amount of the condensed seawater which is discharged from the power recovery device;
a pressure sensor configured to measure a pressure of the seawater which is supplied to the reverse osmosis membrane;
a first flow-amount sensor configured to measure a flow amount of the fresh water which is discharged from the reverse osmosis membrane;
a second flow-amount sensor configured to measure a flow amount of the condensed seawater discharged from the reverse osmosis membrane or a flow amount of the seawater discharged from the booster pump;
a third flow-amount sensor configured to measure a flow amount of the seawater which is supplied to the power recovery device;
a controller that:
controls a valve opening degree of the discharge valve, based on values measured by the pressure sensor and the first flow-amount sensor,
controls a number of revolutions of the booster pump, based on a value measured by the second flow-amount sensor,
controls a valve opening degree of the exhaust valve, based on values measured by the second flow-amount-sensor and the third flow-amount sensor, and
controls the number of revolutions of the booster pump and the valve opening degree of the exhaust valve in such a manner that a difference between the flow amount of the condensed seawater supplied from the reverse osmosis membrane to the power recovery device and the flow amount of the seawater supplied to the power recovery device becomes a predetermined value, wherein the predetermined value is the power consumption of the power recovery device;

a thermometer configured to measure a temperature of seawater supplied to the high-pressure pump and the power recovery device;

an electrical conductivity meter configured to measure an electrical conductivity of the seawater supplied to the high-pressure pump and the power recovery device;

a pH meter configured to measure a pH of seawater supplied to the high-pressure pump and the power recovery device, and a setting module that:
- sets a target flow amount of the booster pump and a recovery ratio, based on values measured by the thermometer and the electrical conductivity meter,
- delivers the target flow amount and the recovery ratio to the controller, and
- corrects the target flow amount and the recovery ratio, based on a value measured by the pH meter.

3. The seawater desalination apparatus of claim 1, further comprising:
- a water feed pump configured to feed seawater to the high-pressure pump and the power recovery device;
- a discharge valve configured to control an amount of seawater which is fed from the water feed pump
- a protection filter provided at a rear stage of the water feed pump;
- a second pressure sensor configured to measure an input pressure of the protection filter;
- a third pressure sensor configured to measure a pressure of seawater which is supplied to the high-pressure pump;
- a fourth pressure sensor configured to measure a pressure of the condensed seawater which is exhausted from the power recovery device; and
- a second controller configured to control a valve opening degree of the discharge valve, based on values measured by the second pressure sensor, the third pressure sensor and the fourth pressure sensor.

4. The seawater desalination apparatus of claim 3, wherein the second controller is configured to control the valve opening degree of the discharge valve in such a manner that the value measured by the fourth pressure sensor becomes a predetermined value or more.

5. The seawater desalination apparatus of claim 3, further comprising an electric power amount meter configured to measure electric power amounts of the high-pressure pump, the booster pump and the water feed pump.

6. The seawater desalination apparatus of claim 2, further comprising:
- a water feed pump configured to feed seawater to the high-pressure pump and the power recovery device;
- a second discharge valve configured to control an amount of seawater which is fed from the water feed pump;
- a protection filter provided at a rear stage of the water feed pump;
- a second pressure sensor configured to measure an input pressure of the protection filter;
- a third pressure sensor configured to measure a pressure of seawater which is supplied to the high-pressure pump;
- a fourth pressure sensor configured to measure a pressure of the condensed seawater which is exhausted from the power recovery device; and
- a second controller configured to control a valve opening degree of the second discharge valve, based on values measured by the second pressure sensor, the third pressure sensor and the fourth pressure sensor.

7. The seawater desalination apparatus of claim 6, wherein the second controller is configured to control the valve opening degree of the second discharge valve in such a manner that the value measured by the fourth pressure sensor becomes a predetermined value or more.

\* \* \* \* \*

UNITED STATES PATENT AND TRADEMARK OFFICE
CERTIFICATE OF CORRECTION

PATENT NO. : 9,145,310 B2  
APPLICATION NO. : 13/104756  
DATED : September 29, 2015  
INVENTOR(S) : Namba et al.

Page 1 of 1

It is certified that error appears in the above-identified patent and that said Letters Patent is hereby corrected as shown below:

Claims

Claim 3, column 11, lines 23-24, change "pump a" to --pump; a--.

Signed and Sealed this  
Twenty-second Day of March, 2016

Michelle K. Lee  
*Director of the United States Patent and Trademark Office*